US006946060B2

(12) United States Patent
Gentilcore

(10) Patent No.: US 6,946,060 B2
(45) Date of Patent: Sep. 20, 2005

(54) PURIFICATION OF N,N-DIMETHYLACETAMIDE

(75) Inventor: Michael J. Gentilcore, Maryland Heights, MO (US)

(73) Assignee: Mallinckrodt Inc., St. Louis, MO (US)

( * ) Notice: Subject to any disclaimer, the term of this patent is extended or adjusted under 35 U.S.C. 154(b) by 244 days.

(21) Appl. No.: 10/186,764

(22) Filed: Jul. 1, 2002

(65) Prior Publication Data

US 2004/0000470 A1 Jan. 1, 2004

(51) Int. Cl.[7] ............................. B01D 3/14; B01D 3/42; C07C 231/24
(52) U.S. Cl. ............................... 203/2; 203/17; 203/78; 203/DIG. 9; 564/216
(58) Field of Search ......................... 203/2, 17, 22–23, 203/25, 27, 73, 78, 80, DIG. 8, DIG. 9; 564/216

(56) References Cited

U.S. PATENT DOCUMENTS

| | | | |
|---|---|---|---|
| 3,419,478 A | * 12/1968 | Izard | 203/70 |
| 3,951,755 A | * 4/1976 | Sartorius et al. | 203/16 |
| 3,959,371 A | 5/1976 | Gavlin et al. | 564/216 |
| 4,177,111 A | * 12/1979 | Pieper et al. | 203/14 |
| 4,576,683 A | * 3/1986 | Cohen | 203/15 |
| 5,124,004 A | 6/1992 | Grethlein et al. | 230/19 |
| 5,180,474 A | 1/1993 | Skatulla et al. | 230/84 |
| 6,159,344 A | 12/2000 | Marion et al. | 202/154 |

FOREIGN PATENT DOCUMENTS

FR 1549711 12/1968

OTHER PUBLICATIONS

Du Pont Company, *Dimethylacetamide Properties, Uses, Storage and Handling*, Literature, Oct. 1988.
Carli et al., *Thermodynamic characterization of vapour–liquid equilibria of mixtures acetic acid–dimethylacetamide and water–dimethylacetamide*, Chemical Engineering Science, 1972, vol. 27, pp. 993–1001.
PCT, *International Search Report*, PCT/US03/19405, mailed Apr. 13, 2004, 5 pages.

* cited by examiner

Primary Examiner—Virginia Manoharan
(74) Attorney, Agent, or Firm—Wood, Herron & Evans, L.L.P.

(57) ABSTRACT

A method to purify N,N-dimethylacetamide (DMAc) from an aqueous solution containing acetic acid as a contaminant. Two fractional distillation columns are arranged in a series. The solution containing the contaminant is provided to the first column with a temperature profile to result in acetic acid partitioning into the overhead water. The material remaining in the bottom portion of the first column is recycled to the first column and also provided into a second column, whereby DMAc free of acetic acid contamination is recovered, and remaining DMAc and acetic acid are returned to the first column for further separation. The method uses standard fractional distillation procedures and equipment, thus eliminating the need for more complex extractions and/or chromatographic separations.

23 Claims, 18 Drawing Sheets

PURIFICATION OF N,N-DIMETHYLACETAMIDE

FIELD OF THE INVENTION

The invention relates generally to a continuous distillation method to purify N,N-dimethylacetamide from a water-N,N-dimethylacetamide feedstock when acetic acid is present as a contaminant.

BACKGROUND

Distillation, a method of separating the components of a solution, depends on the distribution of the components between a gas phase and a liquid phase. The gas phase is produced from the liquid phase by vaporization. A new liquid phase of different composition is produced from the gas phase by condensation.

Continuous distillation is a relatively simple and commonly employed method to separate volatile components of a mixture based upon differences in their boiling points. Continuous distillation is conceptually composed of many ideal stages of distillation, each of which brings together a liquid phase and a gas phase into intimate contact. The components of the liquid phase and gas phase redistribute by condensation and vaporization, and a new liquid phase and new gas phase of different composition leaves the stage. While the change in composition of one stage may be slight, the use of many stages in a countercurrent arrangement can effect a great overall change in composition, and essentially pure component products can result.

Continuous distillation is routinely performed using columns adapted to facilitate contact of the liquid phase and the gas phase by increasing the condensation surface area. For example, columns have incorporated distillation fingers or internals such as sieve plates, bubble caps, and tray valves, which are easily seen as an approximation of an ideal stage. Column internals such as random packing or structured packing do not have clearly defined ideal stages, but are commonly employed for continuous distillation.

The classical configuration for a continuous distillation process is a distillation column with a single condenser overhead and a single reboiler at the bottom. The feedstock is introduced into a nominal middle of the column. The higher boiling components are removed from the reboiler stage as the bottoms product. The lower boiling components are removed from the condenser stage as the distillate. A portion of the distillate is returned (i.e., refluxed) to the top of the column. The reflux liquid contacts the vapors from the reboiler throughout the column to effect the separation. The technology for sizing and designing continuous distillation is well known. Each design is specific to the components that are being separated and to their unique volatility.

In the case of a mixture of N,N-dimethylacetamide (DMAc) and water, separation of the two pure components is simple because of the large difference in volatility, as can be expected from the boiling point for each pure component. The boiling point at atmospheric pressure for DMAc is 166° C. The boiling point at atmospheric pressure for water is 100° C. In a continuous distillation of a DMAc and water feedstock, water will be the distillate from the condenser and DMAc will be the bottoms product from the reboiler.

Acetic acid is often present as a contaminant in the DMAc and water feedstock. This may be because DMAc can degrade to form acetic acid and dimethylamine (DMA). Alternately, acetic acid may be present from a chemical synthesis where DMAc was used as a solvent.

A mixture of DMAc and acetic acid, however, is not easily separated into component parts, even though the boiling point of acetic acid, 118° C., is sufficiently distinct from the boiling point of DMAc. This is due to a hydrogen bonding effect, whereby DMAc, in the presence of acetic acid, acts as a base and exerts a strong attraction for acetic acid. DMAc and acetic acid form a high boiling azeotropic mixture, defined as a solution of two or more liquids, the composition of which does not change upon distillation. More specifically, the azeotrope mixture of 21% acetic acid and 79% DMAc has a boiling point of about 171° C. at atmospheric pressure.

A classical continuous distillation configuration cannot separate mixtures that form azeotropes into two pure component streams. One of the products of the distillation column will approach the azeotrope composition. A high boiling azeotrope, if it occurs, will concentrate in the bottoms product of the reboiler. A low boiling azeotrope, if it occurs, will concentrate in the distillate product of the condenser.

When a mixture of water, DMAc, and acetic acid is fed into a classical distillation column configuration, acetic acid will separate into the bottom of the column, and thereby contaminate the DMAc, because acetic acid will form a high boiling azeotrope with DMAc.

Attempting to remove DMAc as a side-draw vapor stream at or near the bottom of the column is not an effective solution. Acetic acid will eventually build to concentrations in the bottom of the column that approach the DMAc-acetic acid azeotrope. The vapors of the azeotrope will migrate up the column and contaminate the side-draw DMAc vapor stream. The concentration of acetic acid in the bottom of the column could be controlled to a concentration well less than the azeotrope by purging the bottoms of the column. However, this will undesirably result in a large loss of DMAc. Redistilling the bottoms DMAc product to remove DMAc as an overhead product in a second distillation column would require the bottoms of the second column to be purged to control acetic acid below its azeotrope composition, again resulting in substantial loss of the desired DMAc component.

French Patent No. 1,549,711 discloses that the bottoms product of a second column, being a feedstock of DMAc and acetic acid, essentially dry of a third component water, could be fed to a third column operated at a different pressure to change the azeotrope composition. This, however, involves the additional expense and step of a third column. Moreover, the system is not disclosed for separation of DMAc, water, and acetic acid.

A method to overcome the aforementioned problems is therefore desired.

SUMMARY

In one embodiment, the invention is directed to a method of separating N,N-dimethylacetamide (DMAc) from an aqueous DMAc solution containing acetic acid. A first distillation column has a top portion and a bottom portion in relation to a feed port. The bottom portion is further divided into upper, mid, and lower bottom portions. The solution is fed into a first distillation column through a side feed port at the nominal middle of the column.

The column temperature profile is controlled to render the lower bottom portion of the column substantially dry and the upper bottom portion of the column substantially wet, to partition acetic acid between the overhead distillate stream and the bottoms product stream. The bottoms product of the first distillation column is fed to a feed port of a second distillation column to distill purified DMAc to the overhead stream, and to provide a mixture of DMAc and acetic acid into a bottom stream. The bottom stream from the second column enters the entry port of the first column (pumparound) to partition an additional portion of the acetic acid from the mixture of DMAc and acetic acid to the overhead stream of the first column, such that substantially all the acetic acid in the original feed is distilled to the overhead stream of the first column. Purified DMAc is recovered from the overhead portion of the second column.

In another embodiment, the invention is directed to an apparatus to separate fluid components in a feed solution. The apparatus has a first distillation column in series with a second distillation column. The first distillation column has a feed port for a solution, an overhead condenser for an overhead distilled stream, a reboiler for a bottoms stream, and an exit port; the column has top and bottom portions, the bottom portion having upper, mid, and lower bottom portions. The second distillation column has a feed port for the bottom stream from the first column, an overhead condenser for a distilled overhead stream, and a second reboiler for a bottoms product. A pump returns the bottoms product stream from the second column to the feed port of the first column. Control hardware on the first column reflux and the first column reboiler regulates the temperature profile of a column so that the lower bottom portion of the first column is substantially free of the lowest boiling component and the upper bottom portion of the first column is predominantly rich in the lowest boiling component. The temperature profile may be regulated by adjusting heat input to the reboiler or by adjusting the flow rate of reflux returning to the column.

In another embodiment, the invention is directed to a method to purify DMAc from acetic acid in an aqueous solution by feeding the solution into a first distillation column under conditions sufficient to partition aqueous acetic acid into the distillate from the first column, and into the dry non-distillate bottoms product. The bottoms product from the first column is pumped back to an entry port of the first column and also to an entry port of a second distillation column under conditions sufficient to distill purified DMAc as a distillate from the second column, and to provide a non-distillate bottoms product from the second column containing DMAc and acetic acid back to the first column to further partition aqueous acetic acid and DMAc. The return of the second column bottoms product to the first column can be either to the first column feed port at the nominal middle section, the bottoms reboiler, or to another entry port. The bottoms products pumped back to the first column can be to the feed port at the nominal middle section, or to any other entry port located above or within the upper bottom portion of the first column. The purified DMAc is recovered as the distillate from the second column.

The invention is also directed generally to a method to purify a higher boiling component from a solution of a lower boiling component contaminated with a third component that forms a high boiling binary azeotrope with the higher boiling component. The solution is fed into a feed port at a nominal middle section of a first distillation column at a temperature profile sufficient to render the lower bottom portion of the column substantially free of the lower boiling component and to render the upper bottom portion of the first column predominantly rich in the lower boiling component and to partition the third boiling component into the distillate from the first column. The non-distillate bottoms product from the first column is fed to a second distillation column under conditions sufficient to distill the higher boiling component as a pure component from the second column. A portion of the non-distillate bottoms from the first column may also be pumped into a feed port or other entry port of the first column. The non-distillate bottoms product from the second column, containing a mixture of the higher boiling point component and the third component, is fed back through the feed port or other entry port into the first column to further partition the lower and higher boiling point components. This method is generally applicable to systems where the lower boiling component can mitigate the high boiling azeotrope of the higher boiling component with the third component.

These and other embodiments of the invention will be further appreciated in view of the following drawings, description, and example.

DETAILED DESCRIPTION

A method is disclosed to separate acetic acid as a contaminant from an aqueous solution of N,N-dimethylacetamide (DMAc). The method employs continuous distillation techniques using a dual column arrangement. This eliminates the need for more complex solvent extractions and/or chromatographic or spectral separations, and provides efficient, accurate, and reproducible separations with high recovery and high purity of the desired DMAc component.

Figure 1:
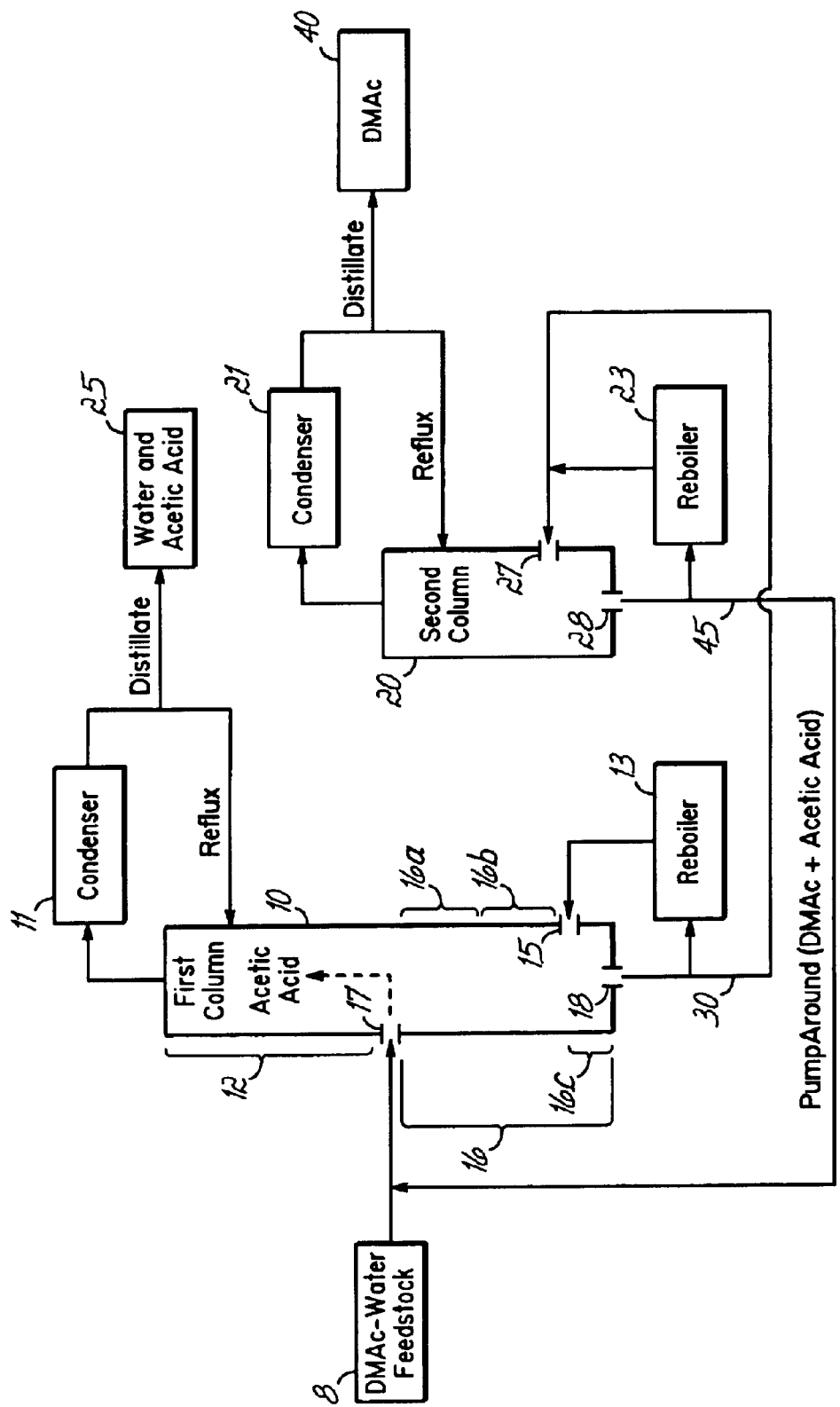
FIG. 1 schematically illustrates the inventive system in use.

With reference to FIG. 1, first 10 and second 20 fractional distillation columns are serially arranged. The first column 10 is schematically divided into top 12 and bottom 16 portions, with a feed or entry port 17 and an exit port 18. The exact location of the feed port 17 is determined by optimal design, as known to one skilled in the art, and is not necessarily the exact mid-point of the column. Thus, the feed port 17 is referred to as located at a nominal middle of the column 10. The bottom 16 portion is further schematically divided into upper bottom 16a, mid-bottom 16b, and lower bottom 16c portions. The specific number of stages constituting the top 12 and bottom 16 portions depend upon the specific column design and the application, as known to one skilled in the art. Examples of these parameters include the feedstock composition, the reflux rate, etc. The second column 20 is arranged so that effluent from the first column 10 enters the second column 20 at entry port 27. The bottoms product of the second column exits at exit port 28.

The first column 10 has a condenser 11 overhead and a reboiler 13 at the bottom. The second column 20 also has a condenser 21 overhead and a reboiler 23 at the bottom. Fluid from exit port 18 of the first column 10 may be pumped directly to entry port 27 of the second column 20. Alternatively, fluid from exit port 18 of the first column 10 may pass through reboiler 23 and then enter the second column 20. Fluid from the exit port 28 of the second column 20 is repumped (pumparound fluid) into the feed port 17 of first column 10.

Generally, all of the incoming acetic acid in the DMAc-water feedstock 8 is purged using a two column arrangement via a DMAc and acetic acid bottoms pumparound and using operating conditions to render the upper bottom 16a portion of the first column 10 wet. More specifically, and with reference to FIG. 1, a mixture of aqueous DMAc to be purified is introduced as a feedstock 8 into the first distillation column 10. The temperature of column 10 is controlled such that a temperature in the upper bottom 16a portion indicates this section of the column is substantially wet, while the lower bottom 16c portion of the first column 10 has a higher temperature and remains substantially dry.

The temperature profile required to effect separation is described as a percentage of the total temperature difference of the temperature of the bottom of the column minus the temperature of the top of the column. Less than about 15% of the total temperature difference in the column occurs in the top portion 12 of the first column 10, less than about 15% of the total temperature difference in the column occurs in the upper bottom 16a portion, and greater than about 70% of the total temperature difference in the column occurs in the mid 16b and lower 16c bottom portions. The exact temperatures, in contrast to the percentage temperature difference, is dependant upon the operating pressure of the first column 10.

The temperature is controlled by adjusting the heat input to the first column reboiler 13, or adjusting the reflux flow rate of distillate on the first column 10. The resulting temperature profile generates a temperature plateau below the feed stage temperature to render the upper bottom portion of the column substantially wet. The wet upper bottom 16a portion is below the feed port 17, and causes a portion of the acetic acid to be stripped overhead to the distillate product 25 of the first column 10. The bottoms product 30 of the first column 10, containing dry DMAc and acetic acid contaminant, is re-fed into the first column 10 through entry port 15 as part of the reboiler 13 arrangement. The bottom product 30 at the first column is also fed into the second column 20 through entry port 27. Pure DMAc is the distilled product 40 of the second column 20. The bottoms product 45 of the second column 20, containing dry DMAc and acetic acid, is returned to the feed port 17 of the first column 10. The bottoms pumparound stream 45 flows through the wet upper bottom 16a portion, which again causes a portion of the acetic acid to be stripped overhead in the first column 10.

The combined effects of stripping a portion of the acetic acid in both the feed 8 and the bottom pumparound 45 results in acetic acid going overhead to the distillate 25 of the first column 10 in a quantity that is equal to all of the acetic acid in the feed 8. Acetic acid in the bottoms of columns 10 and 20 (streams 30 and 45) equilibrates at concentrations well below the azeotrope composition of DMAc and acetic acid, allowing the second column 20 to produce pure DMAc as its distilled product 40.

While particularly described for separating three-component system of DMAc, acetic acid, and water, the invention may be used for any three-component system wherein (a) a first component is a low boiling compound and is present in a substantial portion in a feed stock, that is, at a concentration of at least about 25%; (b) a second component is a high boiling compound relative to the first component and is present in a substantial portion in the feed stock, that is, at a concentration of at least about 5%; (c) a third component is present in a minor portion in the feed stock, that is, at a concentration of at most about 5%, and forms a high boiling azeotrope with the second component; and (d) the first component can cancel, control, or mitigate the two component azeotrope.

Figure 1A:
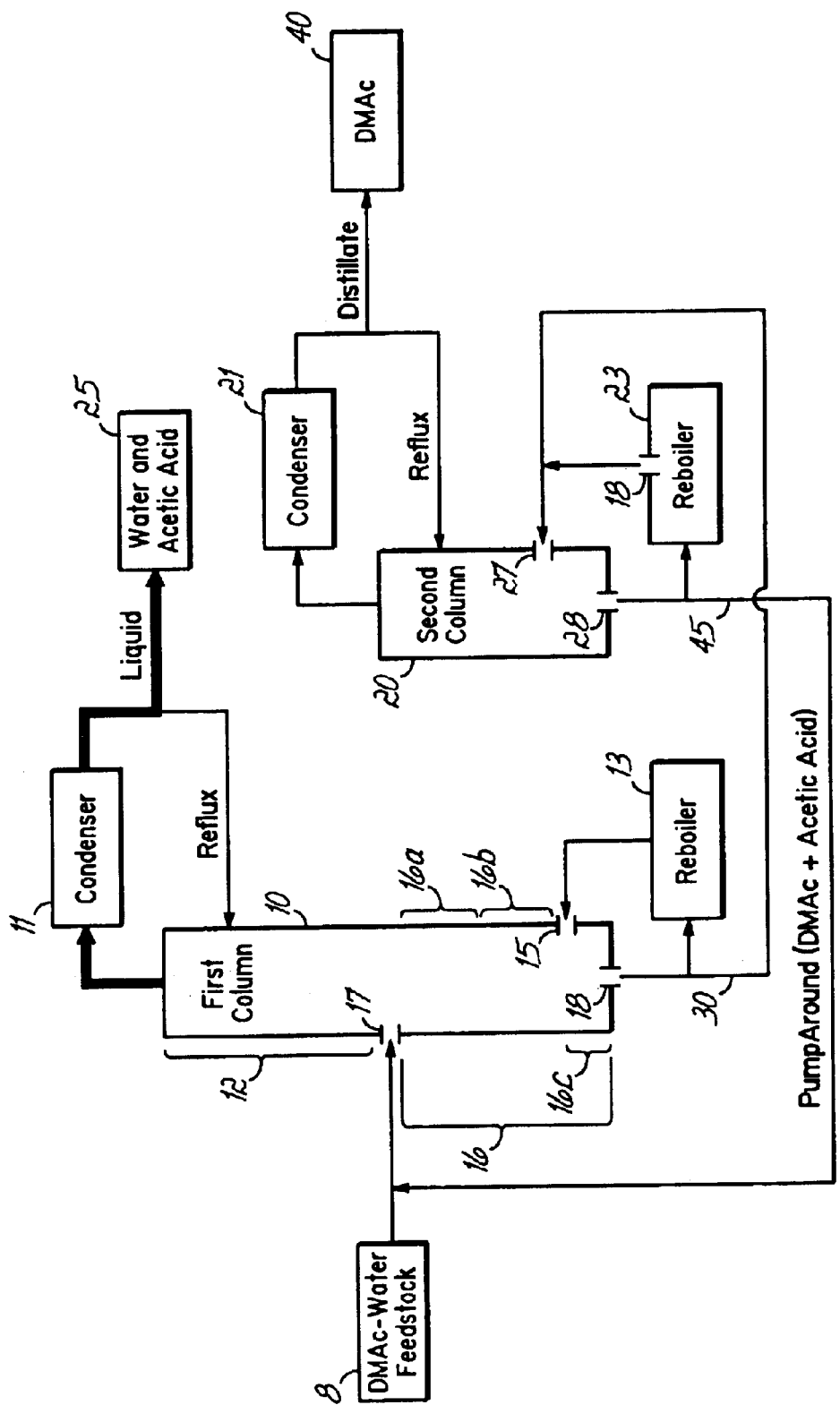
FIGS. 1A–1P schematically illustrate various configurations of the system of FIG. 1.
Figure 1B:
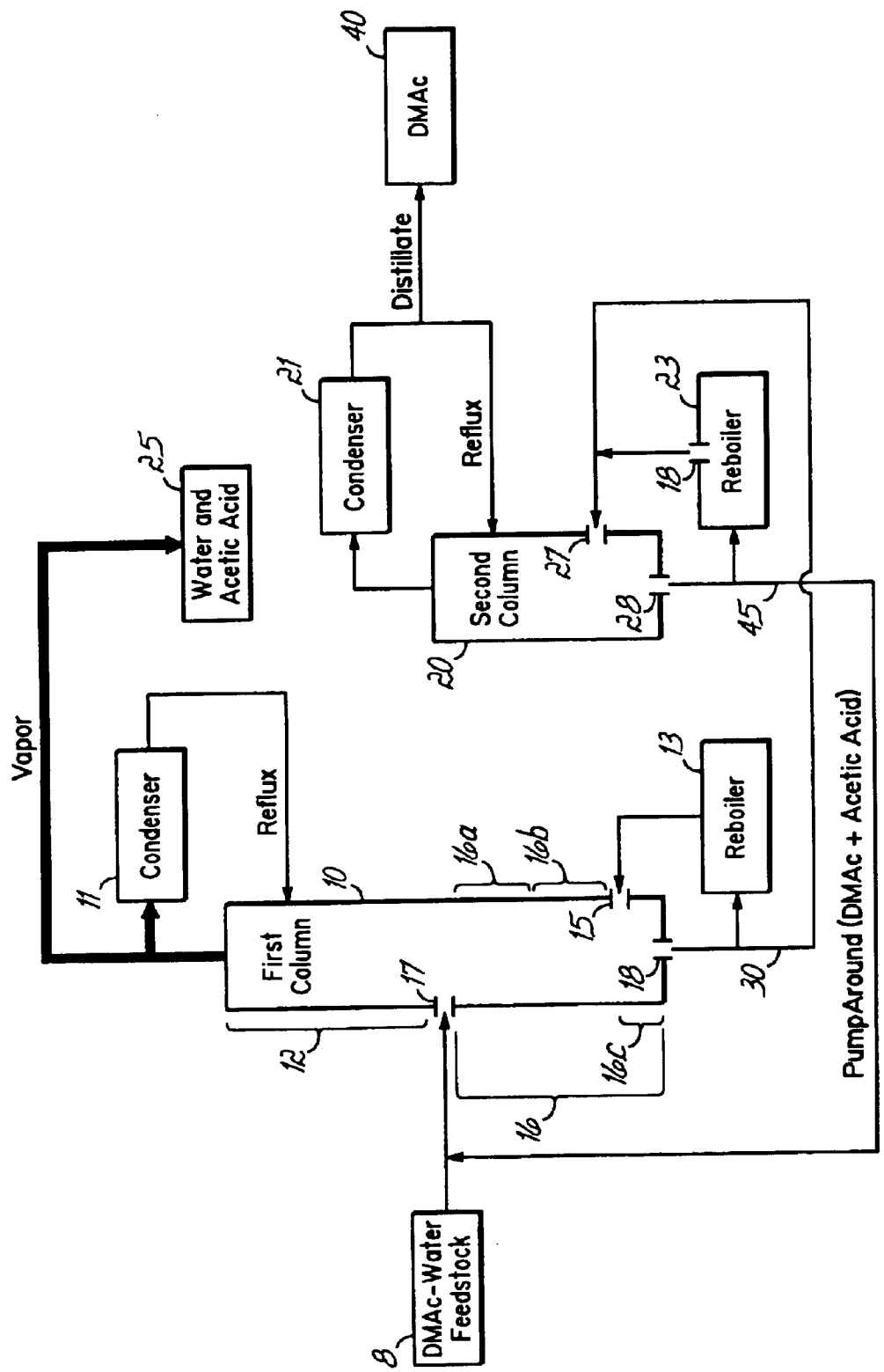
Figure 1C:
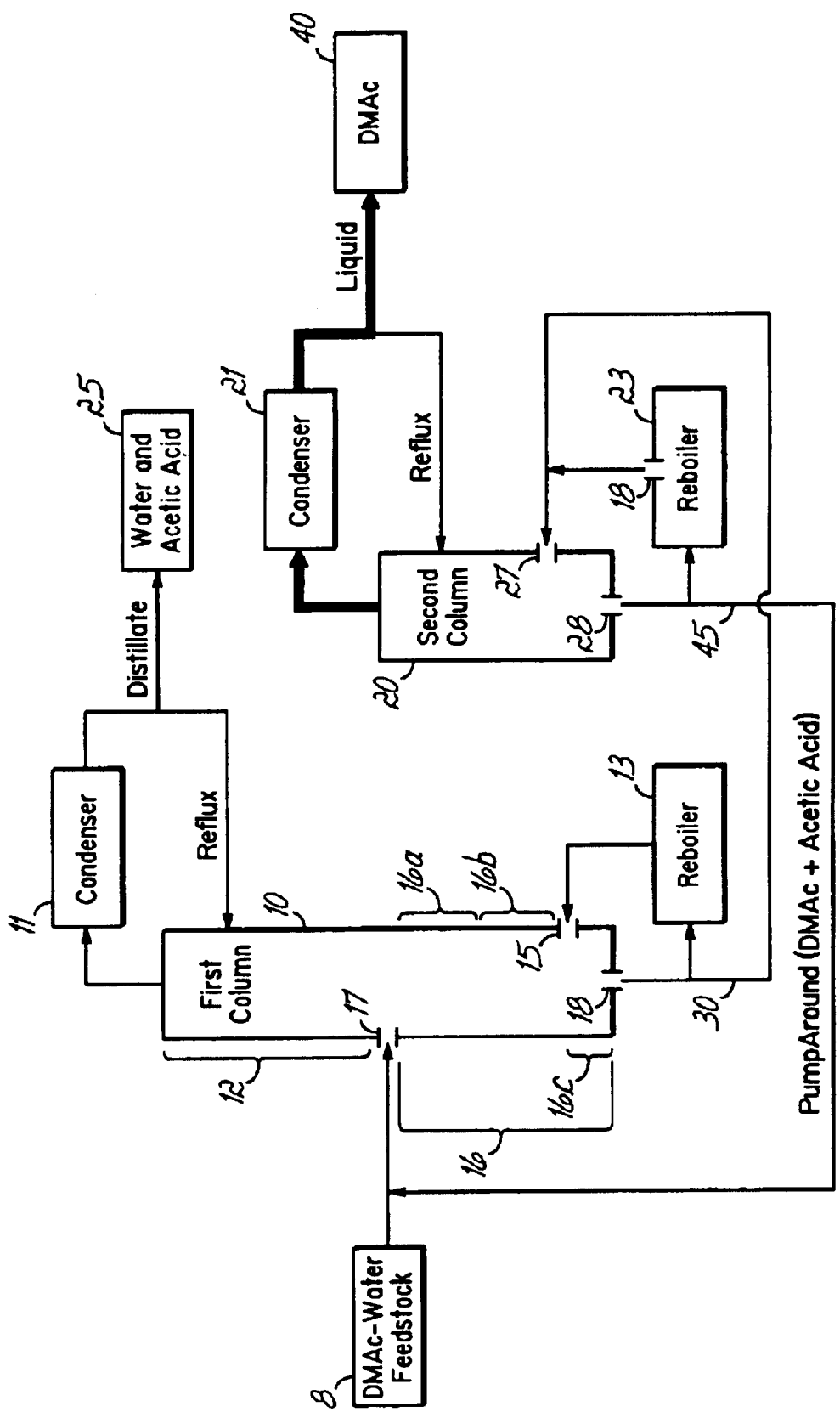
Figure 1D:
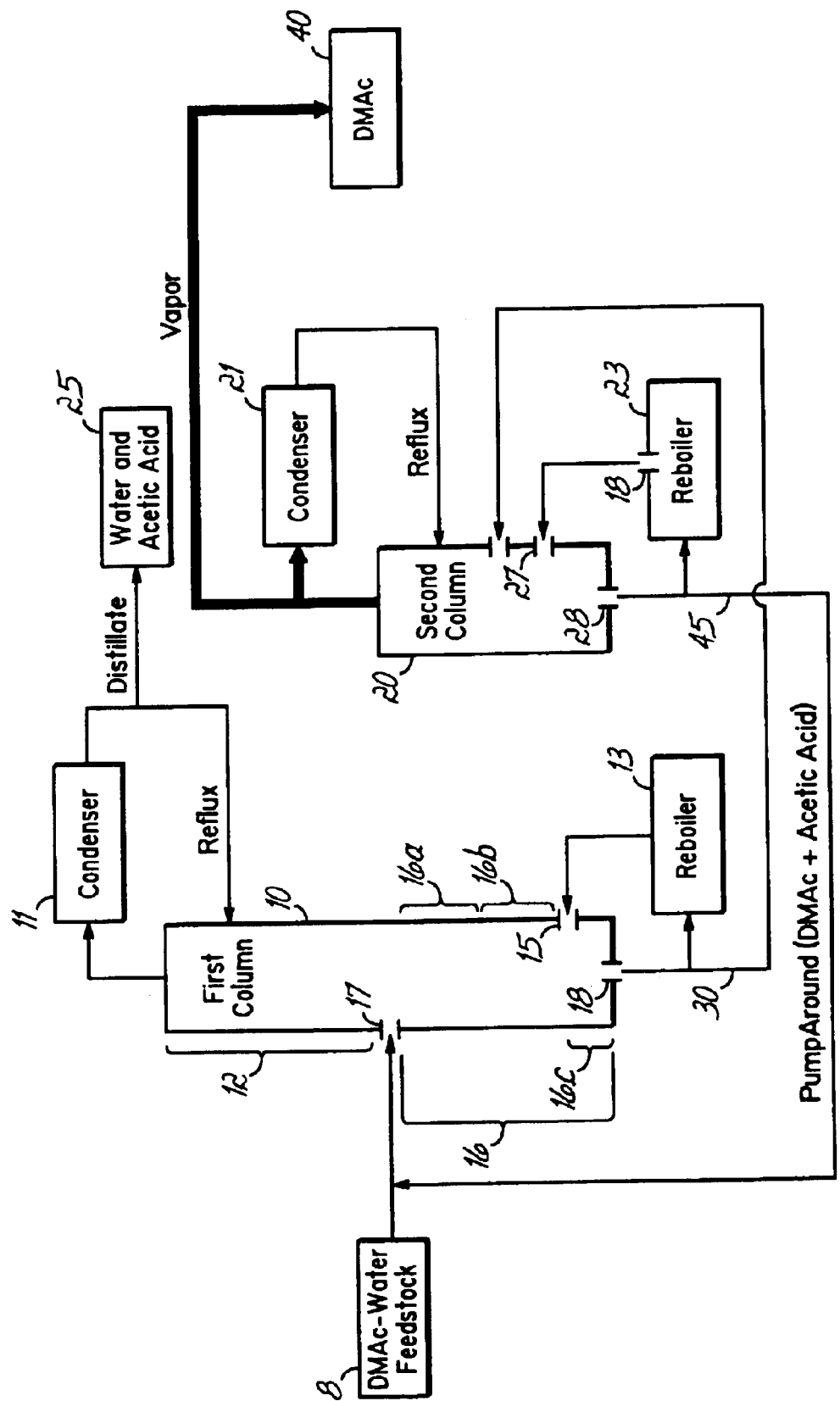
Figure 1E:
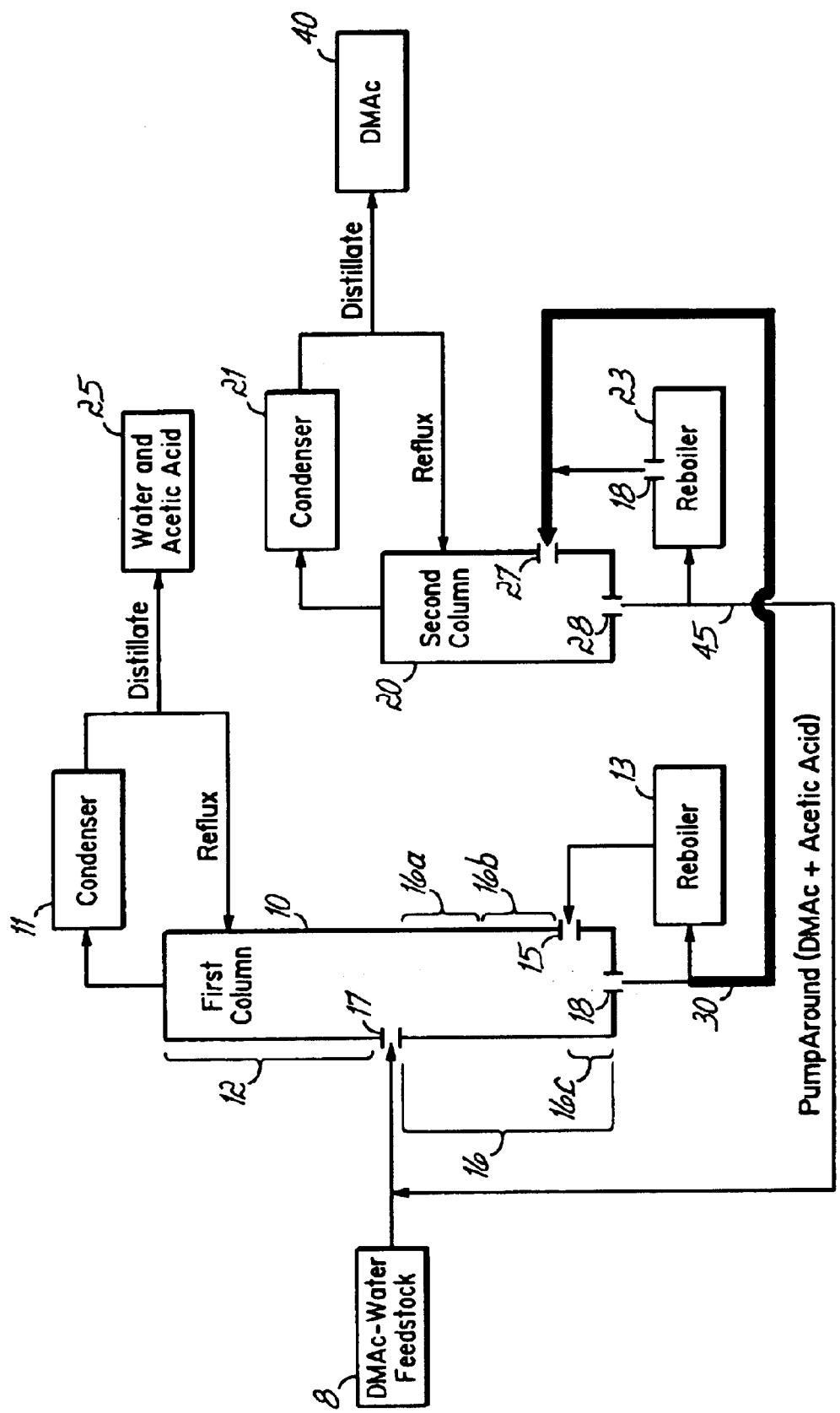
Figure 1F:
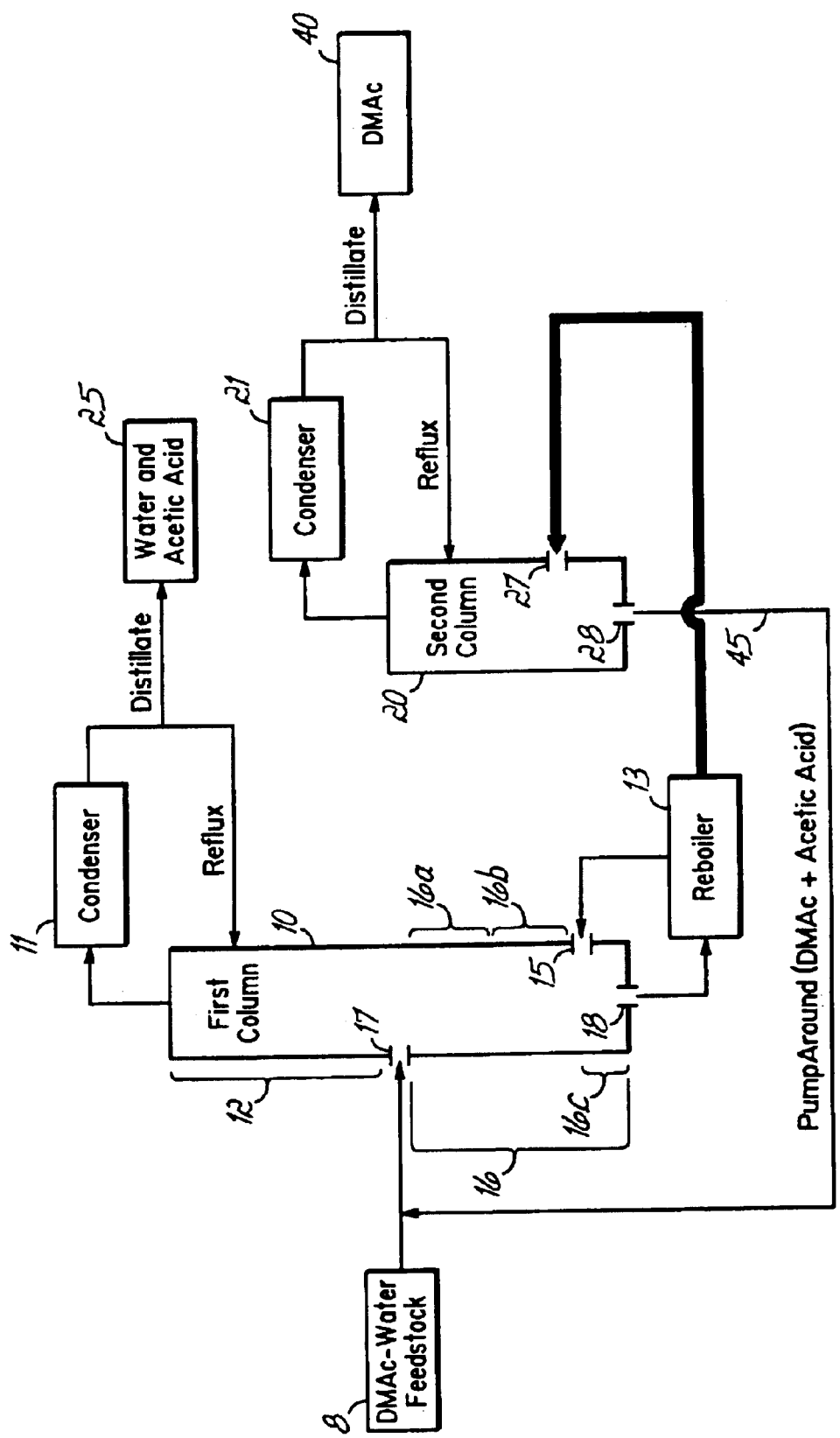
Figure 1G:
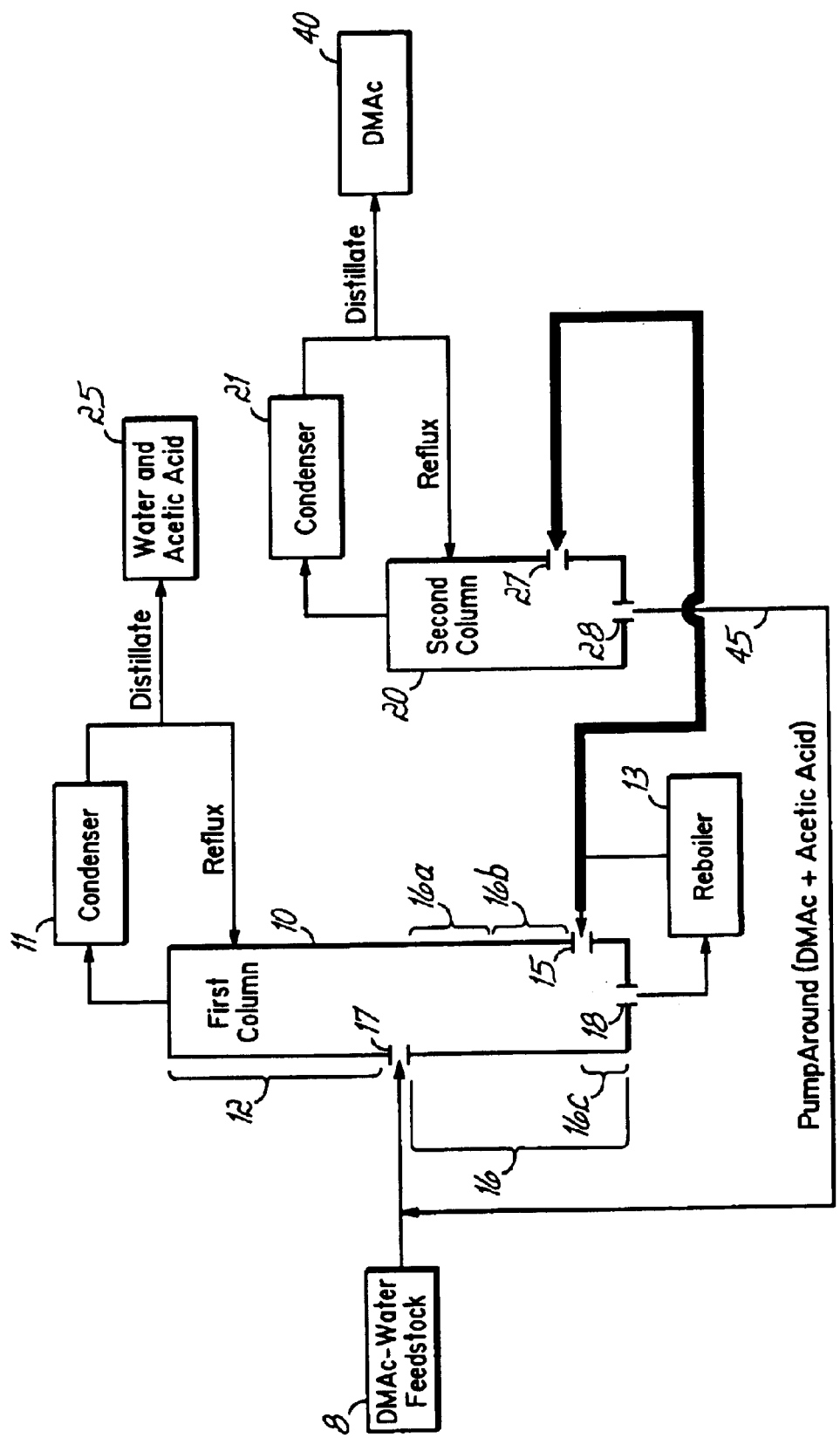
Figure 1H:
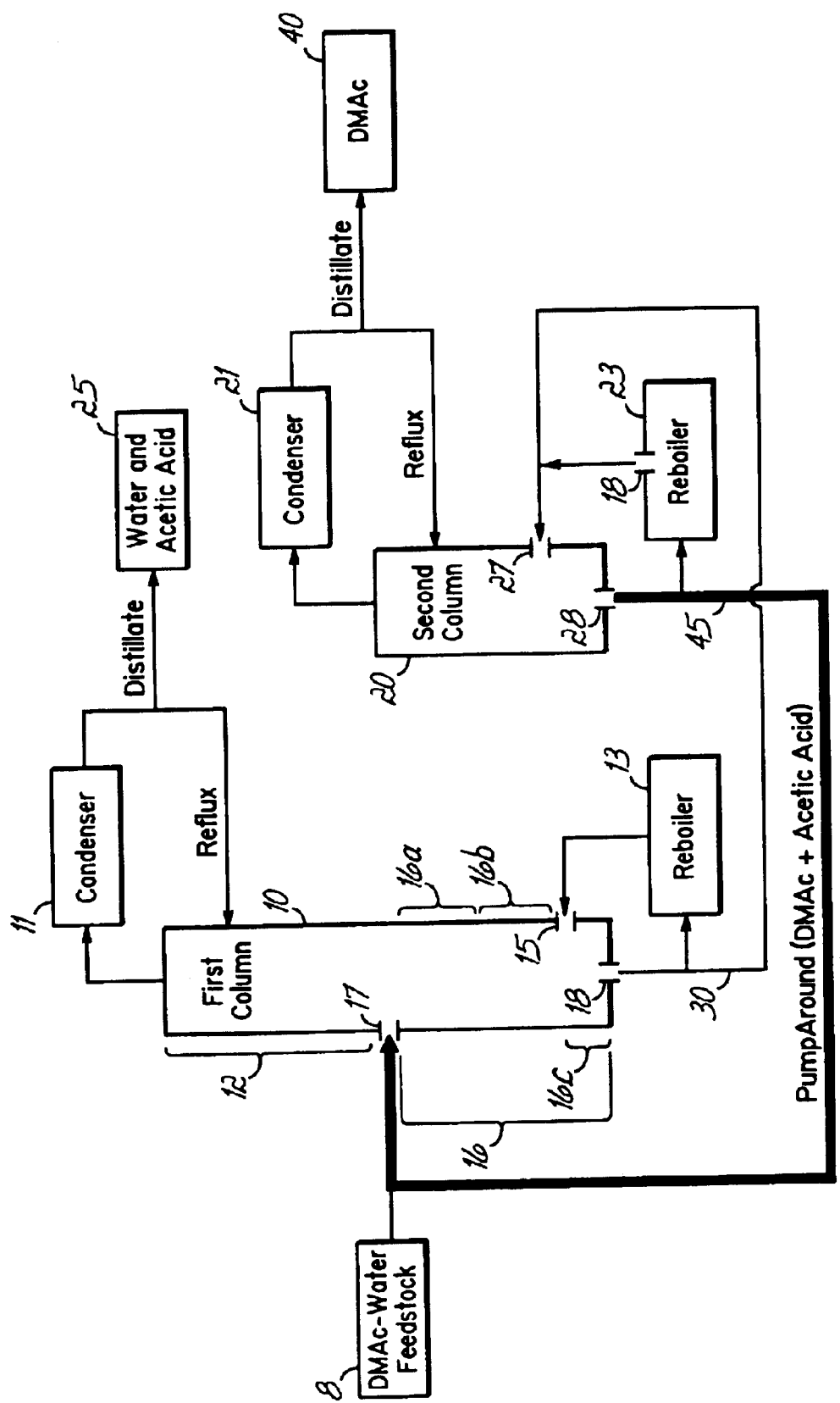
Figure 1J:
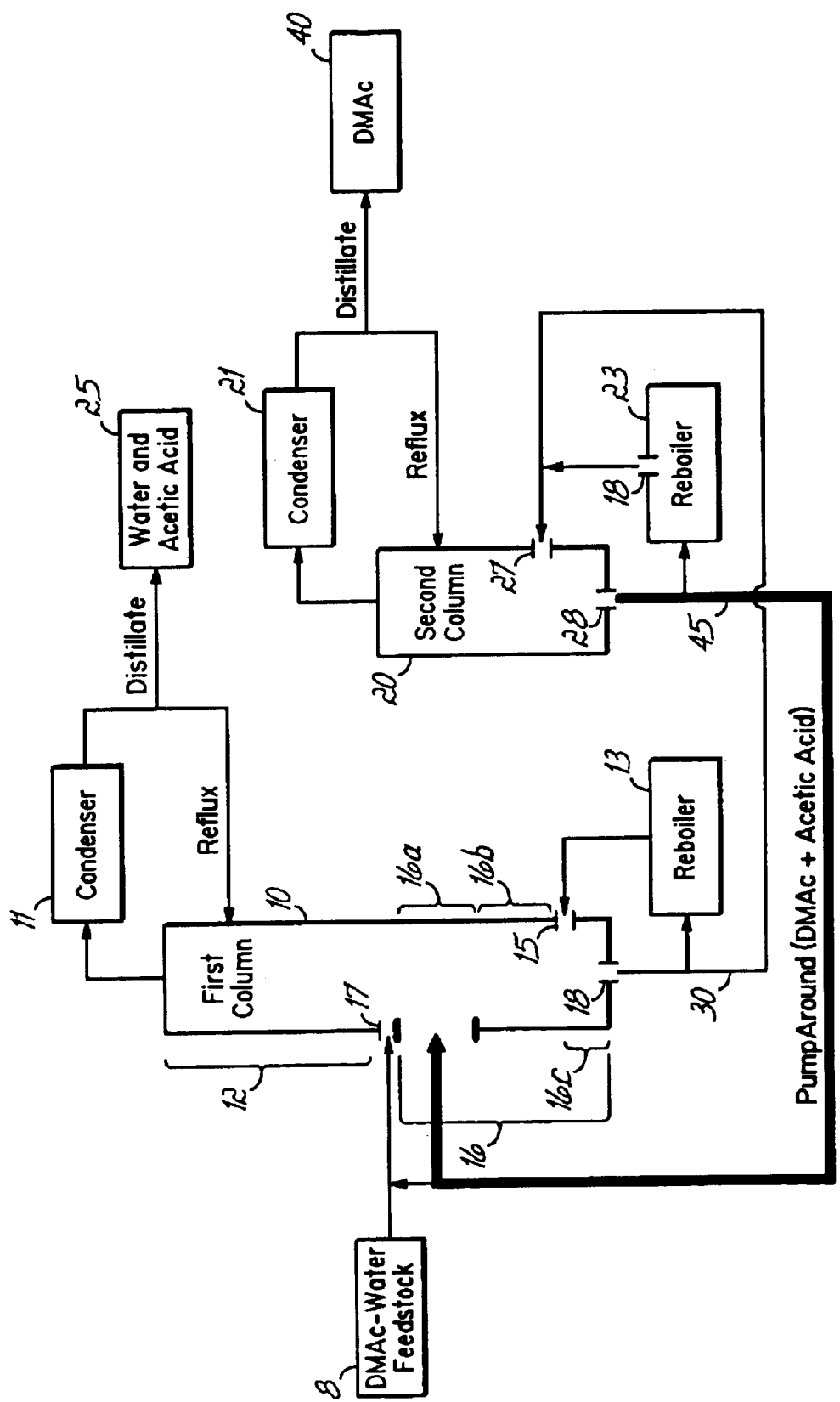
Figure 1K:
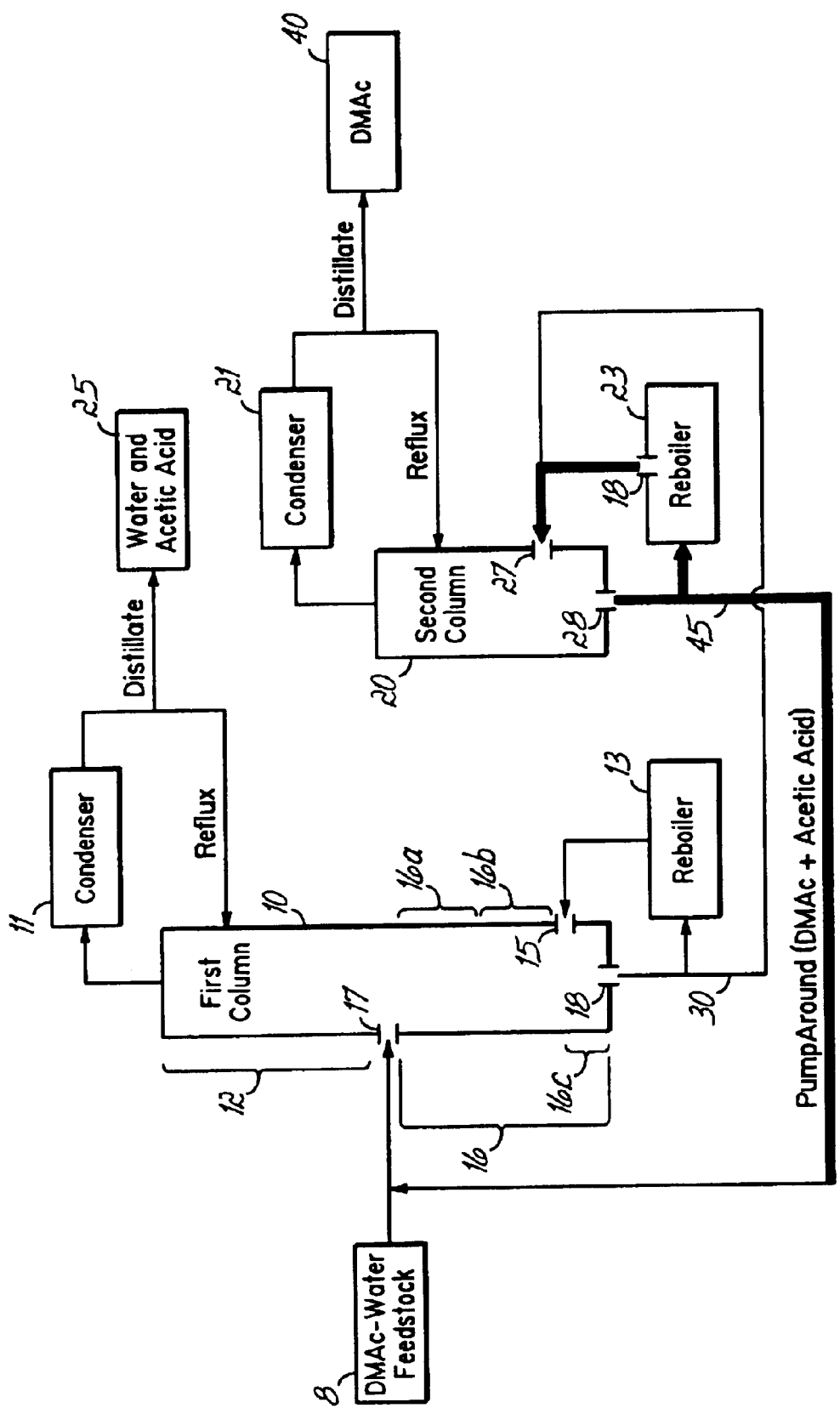
Figure 1L:
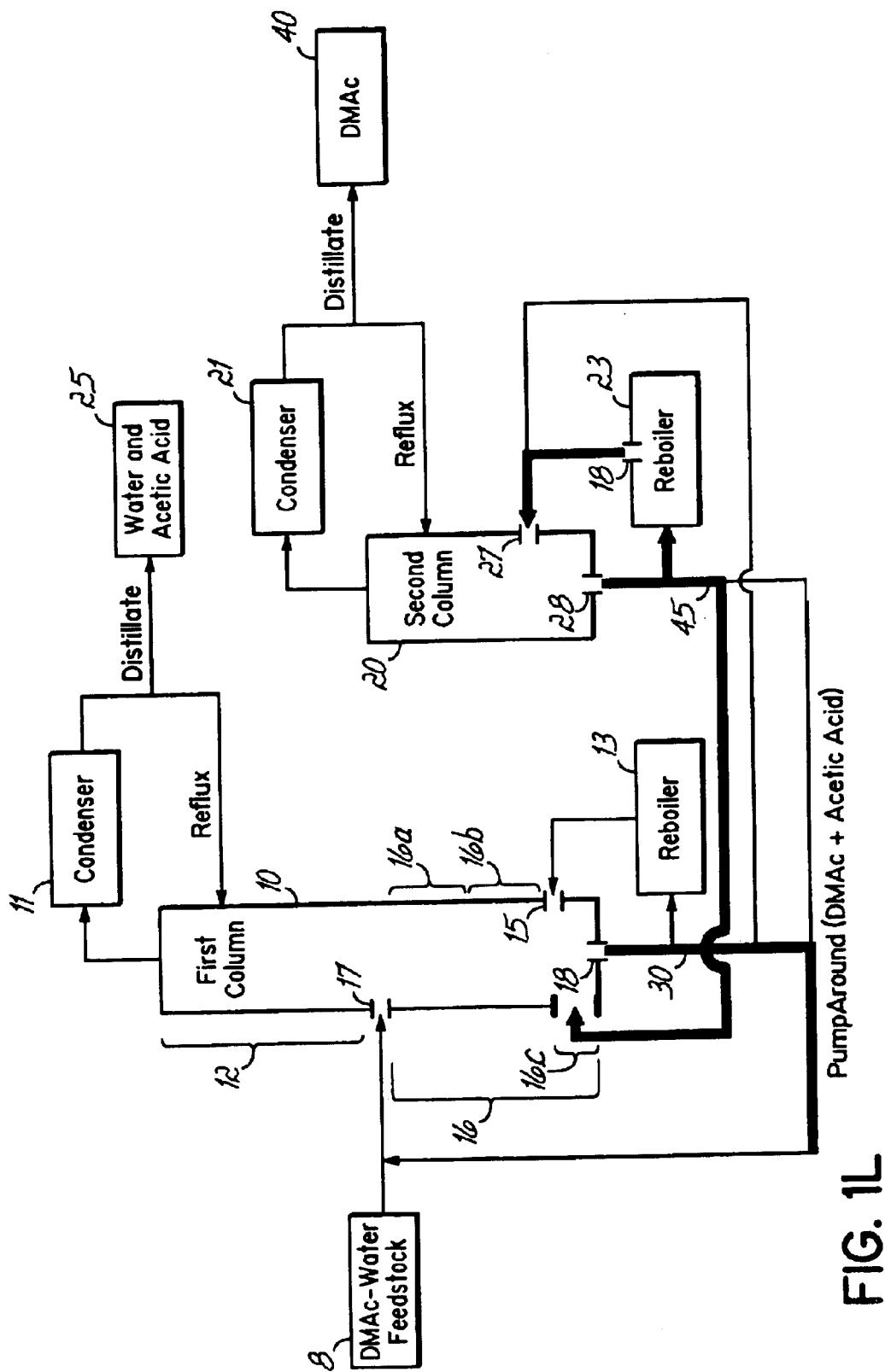
Figure 1M:
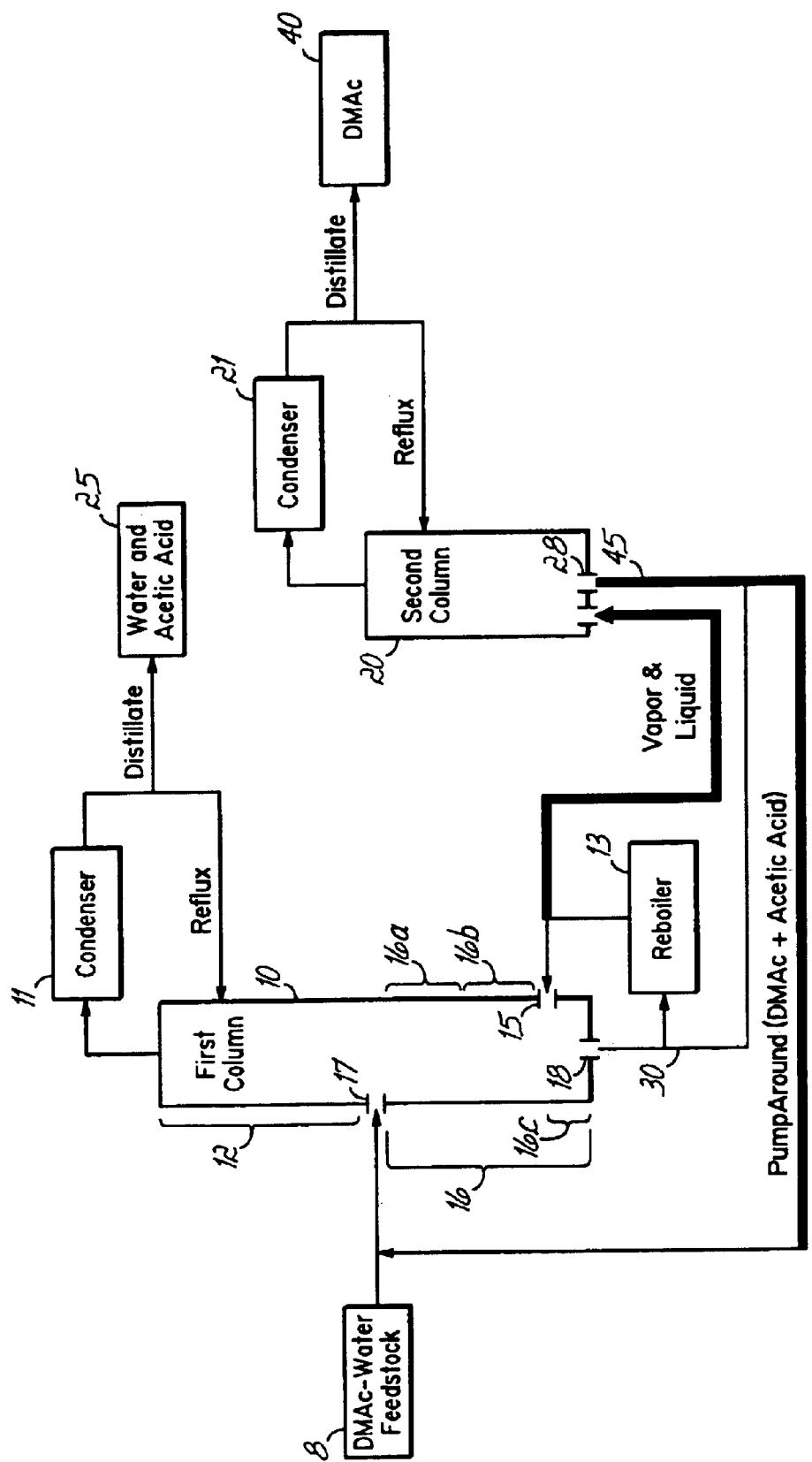
Figure 1N:
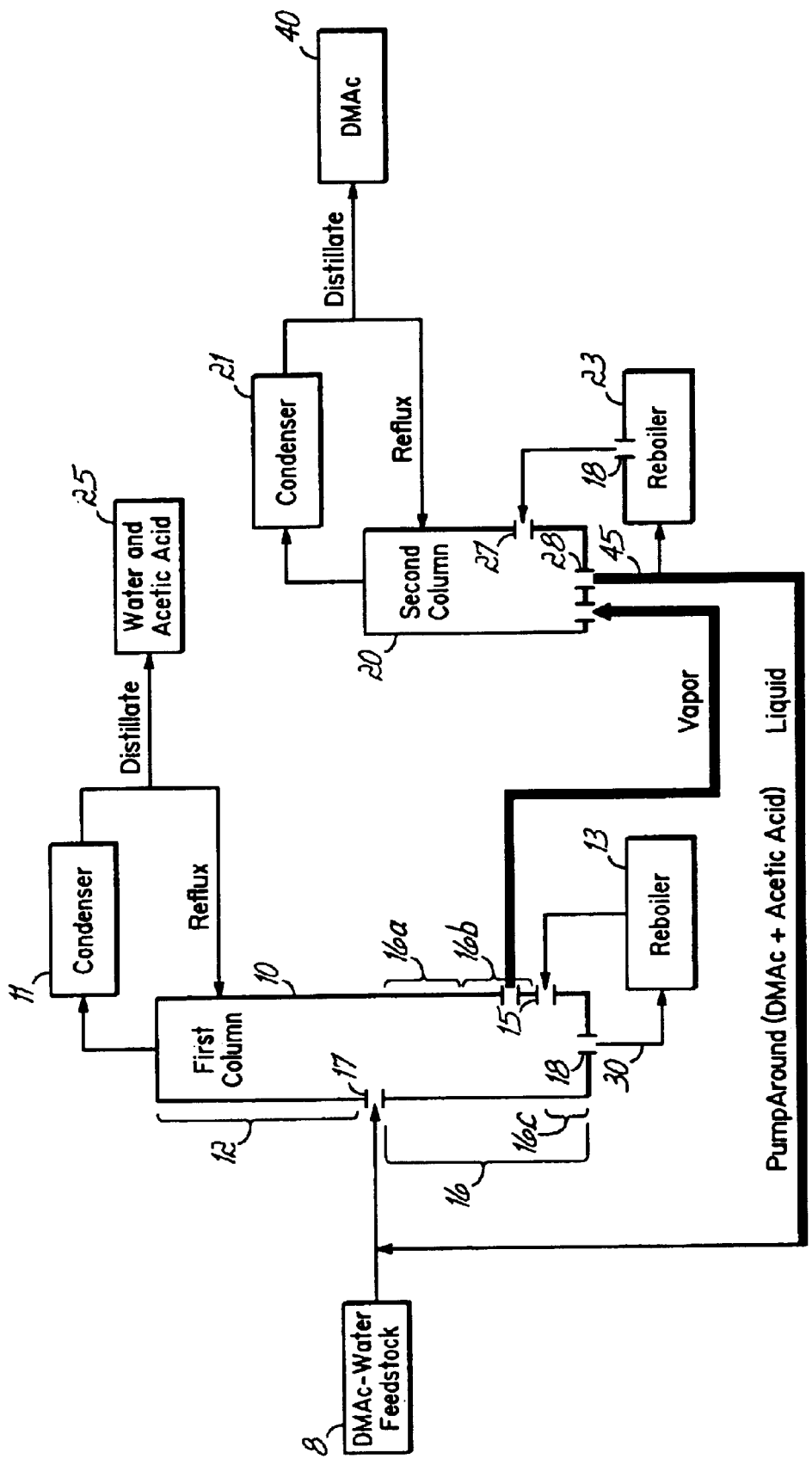
Figure 10:
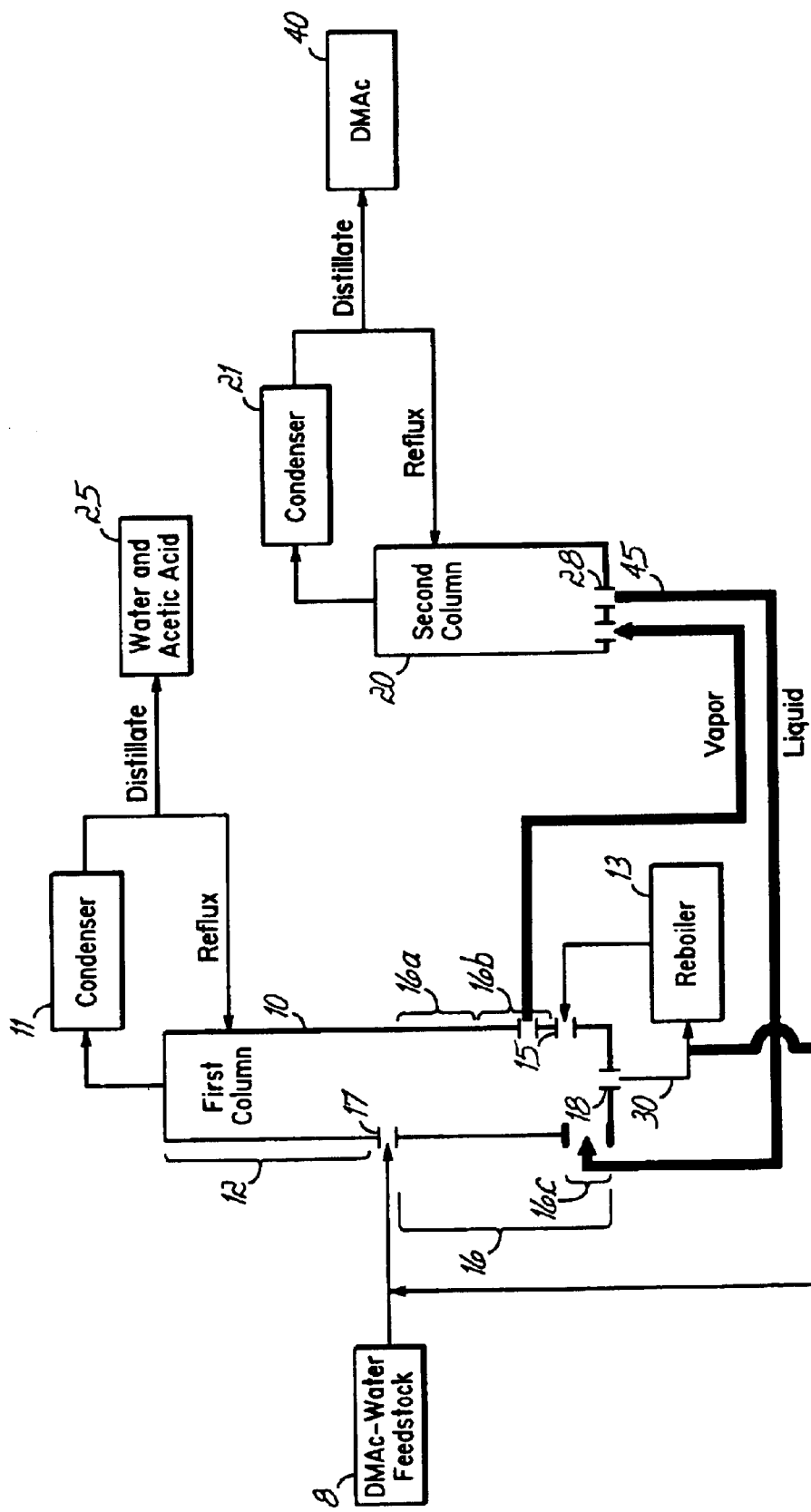
Figure 1P:
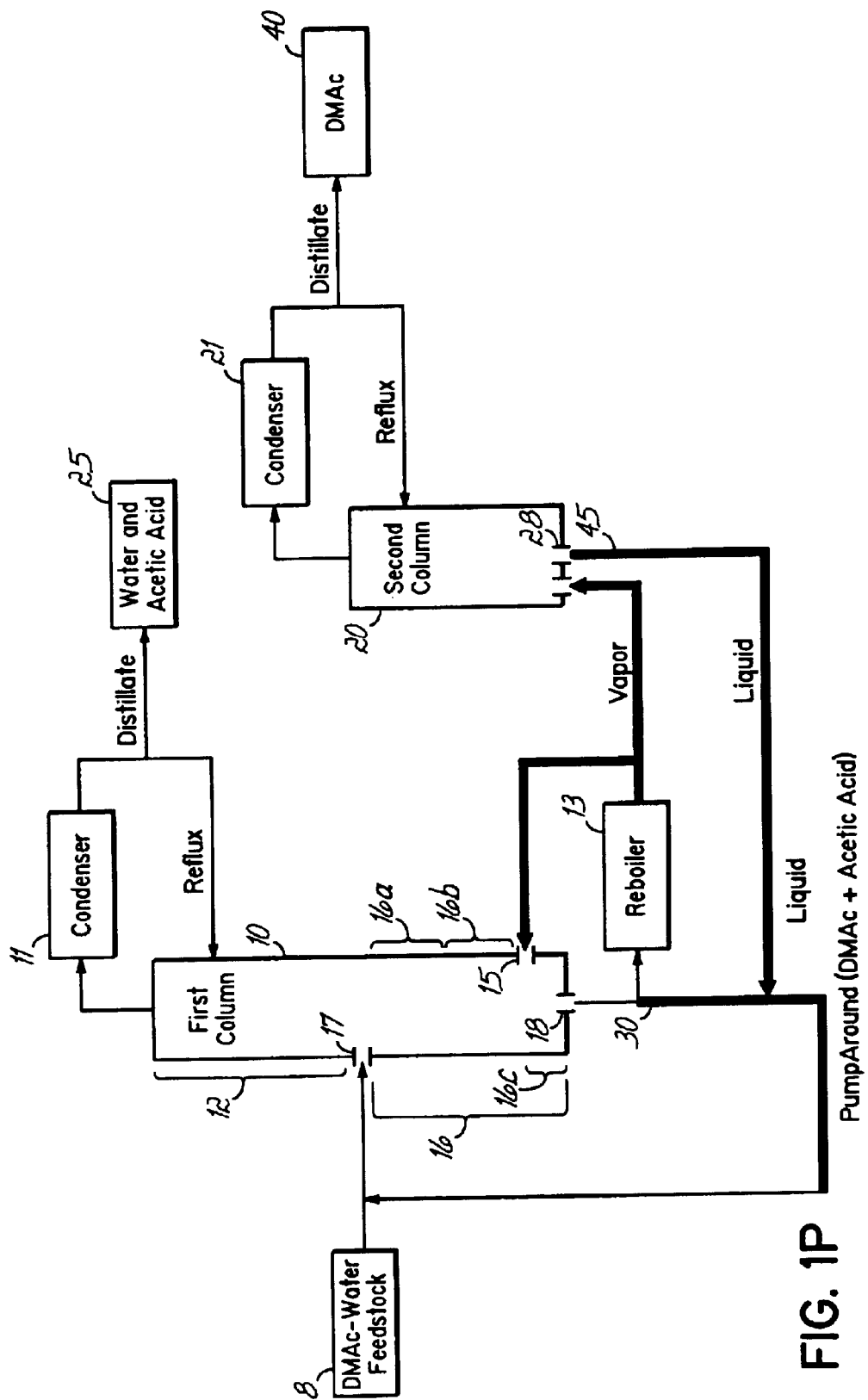

Other configurations of the first and second distillation columns are possible, each of which is within the scope of the invention. As examples, the first column condenser can be total, for removal of the liquid product FIG. 1A, or partial, for removal of the vapor product FIG. 1B. The second column condenser can be total, for removal of the liquid product FIG. 1C, or partial for removal of the vapor product FIG. 1D. As other examples, the bottoms product from the first column can be removed as a liquid FIG. 1E, as a liquid/vapor mix using a common reboiler FIG. 1F, or as a side draw vapor FIG. 1G. As still other examples, the bottoms pumparound stream may be returned to the first column into the feed port FIG. 1H, at an entry port above the feed port FIG. 1I, or at an entry port within the upper bottom portion FIG. 1J. As yet other examples, the bottoms pumparound stream may be obtained from the second column FIG. 1K, or from the first column with the second column bottoms pumparound stream returned to the first column FIG. 1L. As additional examples, the bottoms pumparound stream may be obtained while eliminating the reboiler on the second column by using a reboiler common to the first and second columns FIG. 1M, by a side vapor draw to feed the second column to a pumparound stream FIG. 1N, by a side vapor draw to feed the second column to the first column FIG. 1O, or by a common kettle reboiler FIG. 1P.

EXAMPLE

A temperature profile to render the upper bottom 16a portion of first column 10 wet, using a twenty-six stage, including the reboiler and condenser, continuous distillation process is shown in the following table. In this example, the first column 10 is operated with a top pressure of 103 mm Hg, a bottom pressure of 153 mm Hg, and a pressure drop of 50 mm Hg. The specific temperatures shown in the following table are, however, a function of the pressure at which the first column is operated, and these specific temperatures or pressures are not required. Thus, any temperature and/or pressure which renders the lower bottom portion of the column substantially dry may be used.

| Stage Number | Temperature (° C.) | Pressure (mm Hg) |
|---|---|---|
| 1 | 42.1 | 103.0 Condenser with Subcooling |
| 2 | 54.0 | 113.0 |
| 3 | 54.3 | 114.7 |
| 4 | 54.6 | 116.3 |
| 5 | 54.9 | 118.0 |
| 6 | 55.2 | 119.7 |
| 7 | 55.5 | 121.3 |
| 8 | 55.8 | 123.0 |
| 9 | 56.1 | 124.7 |
| 10 | 56.4 | 126.3 |
| 11 | 56.7 | 128.0 |
| 12 | 57.1 | 129.7 |
| 13 | 57.8 | 131.3 |
| 14 | 59.2 | 133.0 Feed |
| 15 | 59.5 | 134.7 |
| 16 | 59.8 | 136.3 |
| 17 | 60.2 | 138.0 |
| 18 | 62.3 | 139.7 |
| 19 | 73.5 | 141.3 |
| 20 | 95.9 | 143.0 |
| 21 | 109.0 | 144.7 |
| 22 | 112.3 | 146.3 |
| 23 | 113.2 | 148.0 |
| 24 | 113.6 | 149.7 |
| 25 | 113.9 | 151.3 |
| 26 | 114.4 | 153.0 Reboiler |

The total temperature difference in the column was calculated as follows:

| | |
|---|---|
| Bottom of Column | 114.4° C. |
| Top Vapor Prior to Condenser | 54.0° C. |
| Total Temperature Difference | 60.4° C. |

The temperature difference in the top portion of the column was calculated as follows:

| | |
|---|---|
| Feed Stage Temp | 59.2° C. |
| Top Vapor Prior to Condenser | 54.0° C. |
| Upper Temperature Difference | 5.2° C. |

This was recalculated as a percent of total temperature difference as 5.2/60.4=8.6%.

The temperature difference in the upper bottom portion top three stages of bottom portion (16) of the column was calculated as follows:

| | |
|---|---|
| Stage 17 | 60.2° C. |
| Feed Stage | 59.2° C. |
| Upper Bottom Temperature Difference | 1.0° C. |

This was recalculated as a percent of total temperature difference as 1.01/60.4=1.7%.

The temperature difference in the mid- and lower bottom portions were calculated as follows:

| | |
|---|---|
| Bottom of Column | 114.4° C. |
| Stage 17 | 60.2° C. |
| Mid & Lower Bottom Temperature Difference | 54.2° C. |

This was recalculated as a percent of total temperature difference as 54.2/60.4=89.7%.

Figure 2:
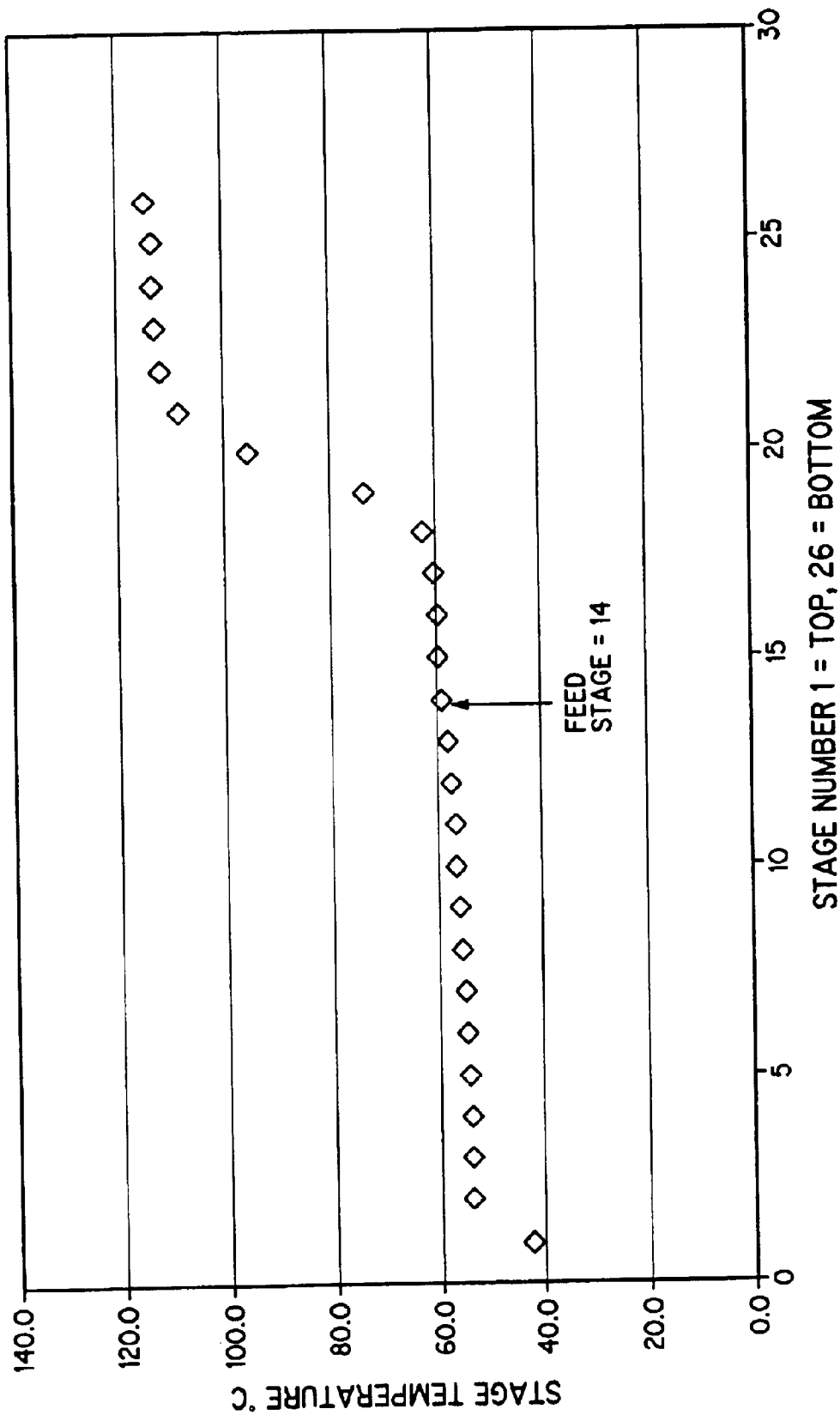
FIG. 2 is a graph of temperatures at each column stage using the inventive system.

The temperature profile graphed in FIG. 2 illustrates the percentage temperature differences in various portions of the column. This graph has a characteristic shape, where there is only a moderate change (i.e., a temperature plateau) in temperatures in the upper bottom 16a portion (stages 15–17 in this example) of the column 10. This characteristic shape occurs regardless of the operating pressure of the column, and is defined in terms of the total temperature difference between the top vapor temperature prior to condensing, and the bottom liquid temperature. This temperature profile produces a wet upper bottom 16a portion to the feed port 17, which results in stripping the acetic acid overhead. In the first column 10, greater than about 70% of the temperature difference occurs in the upper bottom 16a and mid bottom 16b portions (stages 15–20 in this example), less than about 15% of the temperature difference occurs in the lower bottom 16c portion, and less than 15% of the temperature difference occurs in the top portion 12 (stages 2–13 in this example). These conditions result in the lower bottom 16c portion of the first column 10 remaining substantially dry, while the upper bottom 16a portion of the first column 10 remains substantially wet. Under these conditions, the acetic acid contaminant is partitioned between the overhead stream 25 and the bottom stream 30 of the first column 10.

The effluent 30 from the bottom portion 16c of the first column 10 and/or second feed column 45 is recycled back into the feed port 17 of the first column 10 in a pumparound loop. This allows substantially all of the acetic acid to locate in the overhead water 25 of the first column 10.

The material from the lower bottom 16c portion of the first column 10, containing primarily DMAc and acetic acid, is provided to the second column 20 for redistillation. The material may be received in the second column 20 as either liquid or side-draw vapor from the first column. Any acetic acid is present at less than azeotropic concentration, and thus does not negatively affect separation of the DMAc as a pure component 40 and the operation of the second column 20.

Characterization of DMAc in a feedstock resulted in the following parameters in two independent uses of the inventive system. The results were compared to commercially available fresh or virgin DMAc having a concentration of acetic acid at about 80 mg/kg (0.008%):

TABLE 2

| | Assay 1 | Assay 2 |
|---|---|---|
| DMAc Assay | 100.0% | 99.7–99.8% |
| Water Content | <0.01% | <0.01% |
| Acetic Acid Content | <0.01% | 0.2–0.3% |
| Color | <5 units | <5 units |
| Base Fraction as Dimethylamine from all Bases Present | 1–3 mg/kg | 1–3 mg/kg |

Thus, the inventive method yields DMAc which duplicates commercially available DMAc.

It should be understood that the embodiments of the present invention shown and described in the specification are only preferred embodiments of the inventor who is skilled in the art and art not limiting in any way. For example, the method may be used to recover desired lower boiling point products from higher boiling point contaminants by recovering products from the first column distillate. Therefore, various changes, modifications or alterations to these embodiments may be made or resorted to without departing from the spirit of the invention and the scope of the following claims.

What is claimed is:

1. A method of separating N,N-dimethylacetamide (DMAC) from an aqueous DMAc solution containing acetic acid comprising
   (a) providing said solution to a first distillation column, said column having a feed port and an exit port, and having top and bottom portions, said bottom portion having upper, mid, and lower bottom portions, at a temperature sufficient to render the lower bottom portion of the column substantially dry and the upper bottom portion of the column substantially wet, and to partition acetic acid between an overhead stream and a bottom stream of the first column,
   (b) providing the bottom stream of the first column to an entry port of a second distillation column to partition purified DMAc into an overhead stream and a mixture of DMAc and acetic acid into a bottom stream, and
   (c) partitioning an additional portion of the acetic acid from the mixture of DMAc and acetic acid to the overhead stream of the first column.

2. The method of claim 1 further comprising recovering the purified DMAc from the overhead stream of the second column.

3. The method of claim 2 wherein the DMAc is recovered as a liquid from the overhead of the second column.

4. The method of claim 2 wherein the DMAc is recovered as a vapor from the overhead of the second column.

5. The method of claim 1 wherein a temperature profile results in
   <about 15% of the total temperature difference in the first column occurs in the top portion, <about 15% of the total temperature difference in the first column occurs in the upper bottom portion, and >about 70% of the total temperature difference in the first column occurs in the mid and lower bottom portions.

6. The method of claim 5 wherein the temperature is a function of a pressure at which the first column is operating.

7. The method of claim 1 wherein the bottom stream from the second column is provided as a pumparound stream to the first column.

8. The method of claim 7 wherein the bottom stream of the first column is provided as a liquid feed to the second column.

9. The method of claim 7 wherein the bottom stream of the first column is provided as a vapor to the second column.

10. The method of claim 7 wherein the bottom pumparound stream is provided to the first column at the feed port.

11. The method of claim 7 wherein the bottom pumparound stream is provided to the first column at an entry port above the feed port.

12. The method of claim 7 wherein the bottom pumparound stream is provided to the first column at an entry port in the upper bottom portion.

13. The method of claim 7 wherein the bottom pumparound stream is obtained using a reboiler common to the first and second columns.

14. The method of claim 1 wherein the bottom stream of the second column contains acetic acid at less than an azeotrope concentration.

15. The method of claim 1 wherein the acetic acid partitioned in the overhead stream of the first column is recovered as a liquid.

16. The method of claim 1 wherein the acetic acid partitioned in the overhead stream of the first column is recovered as a vapor.

17. The method of claim 1 wherein the bottom stream of the first column is provided to the second distillation column in a physical state selected from the group consisting of a liquid, a vapor, and a liquid/vapor mixture.

18. The method of claim 1 whereby the additional portion of acetic acid is provided by the bottom stream of the second column.

19. The method of claim 1 whereby the additional portion of acetic acid is partitioned by providing a bottom pumparound stream from the first column after a bottom stream from the second column is returned to the first column.

20. A method to purify N,N-dimethylacetamide (DMAc) from acetic acid in an aqueous solution comprising
   providing said solution to a feed port of a first distillation column under conditions sufficient to partition aqueous acetic acid as a distillate from the first column,
   providing a pumparound of a non-distillate bottoms product from a bottom of the first column to the first column feed port and to a second distillation column under conditions sufficient to distill substantially purified DMAc as a distillate from the second column, and
   providing a non-distillate bottoms product from the second column containing DMAc and acetic acid to the first column to further partition aqueous acetic acid to the overhead of the first column, and separating DMAc to the bottoms of the first column.

21. The method of claim 20 further comprising recovering substantially pure DMAc as the distillate from the second column.

22. The method of claim 20 wherein the conditions comprise a temperature profile sufficient to render a lower bottom portion of the first column substantially dry.

23. The method of claim 20 wherein a temperature profile generates a temperature plateau below a feed stage temperature to render an upper bottom portion of the first column substantially wet.

* * * * *

UNITED STATES PATENT AND TRADEMARK OFFICE
CERTIFICATE OF CORRECTION

PATENT NO. : 6,946,060 B2
DATED : September 20, 2005
INVENTOR(S) : Gentilcore

It is certified that error appears in the above-identified patent and that said Letters Patent is hereby corrected as shown below:

Column 5,
Lines 21-22, "The exact temperatures, in contrast to…, is dependant…" should be
-- The exact temperatures, in contrast to…, are dependant … --.

Figure 11:
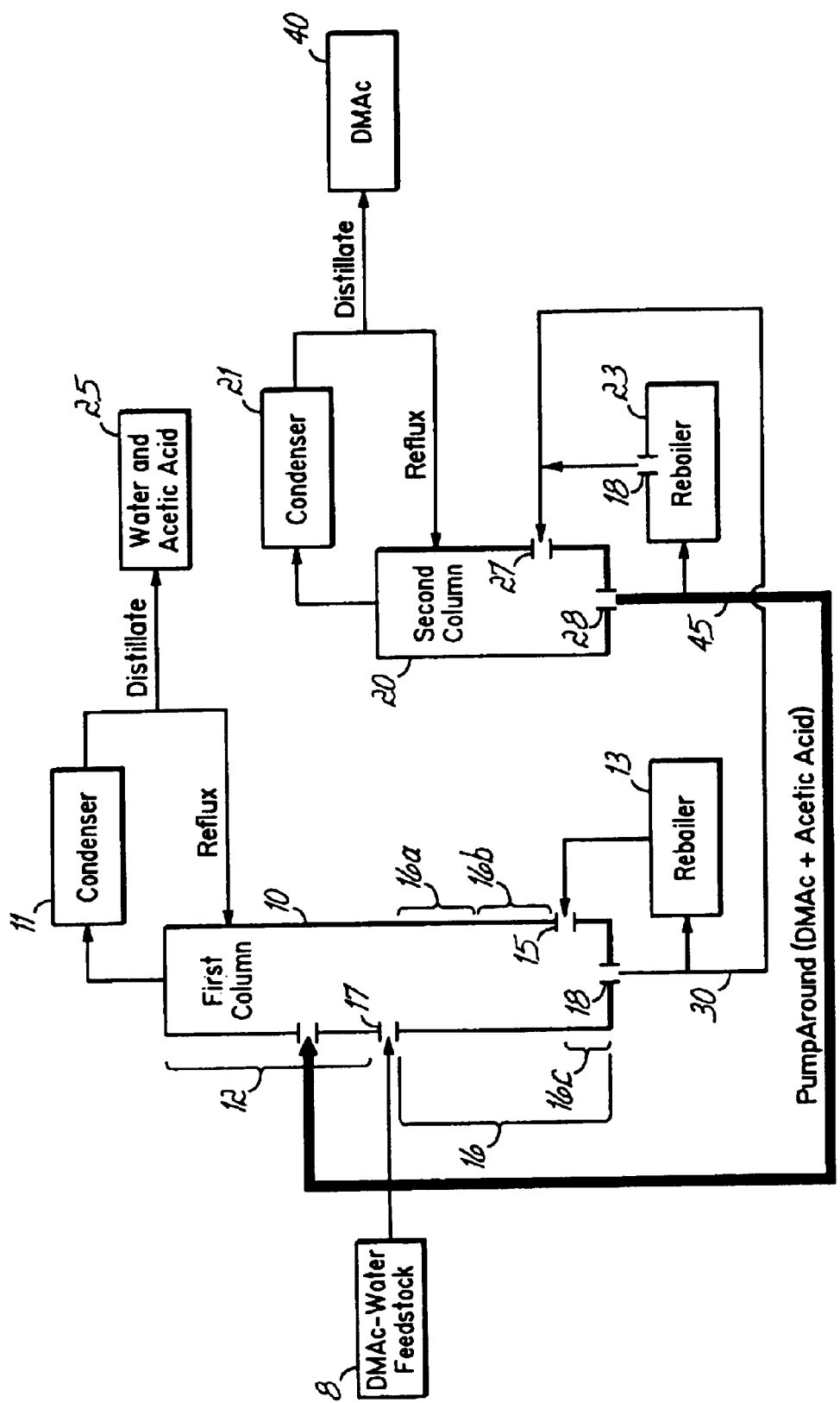

Column 6,
Line 14, "…feed port FIG. 11, or at…" should be -- feed port FIG. 1I --.

Column 8,
Line 29, "…skilled in the art and art not limiting…" should be -- …skilled in the art and are not limiting… --.
Line 39, "…(DMAC) from an aqueous…" should be -- …(DMAc) from and aqueous… --.

Column 10,
Line 26, "…substantially pure DMAc as the…" should be -- …substantially purified DMAc as the… --.

Signed and Sealed this

Twenty-fifth Day of April, 2006

JON W. DUDAS
*Director of the United States Patent and Trademark Office*

US006946060C1

(12) EX PARTE REEXAMINATION CERTIFICATE (5943rd)
United States Patent
Gentilcore

(10) Number: US 6,946,060 C1
(45) Certificate Issued: Oct. 9, 2007

(54) PURIFICATION OF N,N-DIMETHYLACETAMIDE

(75) Inventor: Michael J. Gentilcore, Maryland Heights, MO (US)

(73) Assignee: Malinckrodt Inc., St. Louis, MO (US)

Reexamination Request:
No. 90/007,967, Mar. 10, 2006

Reexamination Certificate for:
Patent No.: 6,946,060
Issued: Sep. 20, 2005
Appl. No.: 10/186,764
Filed: Jul. 1, 2002

Certificate of Correction issued Apr. 25, 2006.

(51) Int. Cl.
*B01D 3/014* (2006.01)
*B01D 3/042* (2006.01)
*C07C 231/024* (2006.01)
*C07C 231/00* (2006.01)
*C07C 233/00* (2006.01)
*C07C 233/05* (2006.01)

(52) U.S. Cl. .............................. 203/2; 203/17; 203/78; 203/DIG. 9; 564/216

(58) Field of Classification Search ....................... None
See application file for complete search history.

(56) References Cited

U.S. PATENT DOCUMENTS 3,687,820 A  8/1972  Akell et al. .................... 203/78
4,506,334 A * 3/1985  DiBiano ........................ 700/270

OTHER PUBLICATIONS

Exhibit B, European Patent Office, *European Search Report In Application No. 03737193*, Feb. 6, 2005, 3 pages.

* cited by examiner

*Primary Examiner*—Jerry D. Johnson

(57) ABSTRACT

A method to purify N,N-dimethylacetamide (DMAc) from an aqueous solution containing acetic acid as a contaminant. Two fractional distillation columns are arranged in a series. The solution containing the contaminant is provided to the first column with a temperature profile to result in acetic acid partitioning into the overhead water. The material remaining in the bottom portion of the first column is recycled to the first column and also provided into a second column, whereby DMAc free of acetic acid contamination is recovered, and remaining DMAc and acetic acid are returned to the first column for further separation. The method uses standard fractional distillation procedures and equipment, thus eliminating the need for more complex extractions and/or chromatographic separations.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–23 is confirmed.

* * * * *